(12) United States Patent
Yang et al.

(10) Patent No.: US 8,597,928 B2
(45) Date of Patent: Dec. 3, 2013

(54) BACTERIOPHAGE OF THE SIPHOVIRIDAE FAMILY AND ANTIBACTERIAL COMPOSITIONS COMPRISING THE SAME

(75) Inventors: Si Yong Yang, Incheon (KR); Soo An Shin, Seoul (KR); Min Tae Park, Incheon (KR); Young Wook Cho, Seoul (KR); In Hye Kang, Suwon-si (KR); Eun Mi Shin, Incheon (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/331,639

(22) Filed: Dec. 20, 2011

(65) Prior Publication Data
US 2012/0156174 A1 Jun. 21, 2012

Related U.S. Application Data

(60) Provisional application No. 61/425,553, filed on Dec. 21, 2010.

(51) Int. Cl.
*A01N 63/00* (2006.01)
*C12N 7/00* (2006.01)
*C12N 1/00* (2006.01)

(52) U.S. Cl.
USPC ............ 435/235.1; 424/93.6; 435/243

(58) Field of Classification Search
None
See application file for complete search history.

(56) References Cited

U.S. PATENT DOCUMENTS

| 6,485,902 | B2 | 11/2002 | Waddell et al. |
| 6,942,858 | B1 | 9/2005 | Ghanbari et al. |
| 2004/0213765 | A1 | 10/2004 | Fischetti et al. |
| 2010/0135962 | A1 | 6/2010 | Kang et al. |
| 2010/0158870 | A1 | 6/2010 | Kang et al. |
| 2010/0166709 | A1 | 7/2010 | Kang et al. |

OTHER PUBLICATIONS

Ackermann, H.W., "Frequency of morphological phage descriptions in the year 2000", Arch Virol (2001) 146:843-857.
Johnson, D.E. et al., "Nutrient Digestibility of Brewers Single Cell Protein", J Anim Sci 1983, 56:735-739.
Slyter, Leonard L., "Influence of Acidosis on Rumen function", J Anim Sci 1976, 43:910-929.
O'Flynn, G. et al., "The newly isolated lytic bacteriophages stl04a and stl04b are highly virulent against *Salmonella enterica*" Journal of Applied Microbiology, vol. 101, pp. 251-259, May 4, 2006.
International Search Report & Written Opinion from PCT/KR2011/009964, dated Jun. 22, 2012.

*Primary Examiner* — Nicole Kinsey White
(74) *Attorney, Agent, or Firm* — Lathrop & Gage LLP; Brian C. Trinque; Andrew T. Wilkins

(57) ABSTRACT

The present invention relates to a novel bacteriophage, more particularly, a bacteriophage that has a specific bactericidal activity against *Salmonella enteritidis*, *Salmonella typhimurium*, *Salmonella gallinarum* and *Salmonella pullorum*, a composition for the prevention or treatment of infectious diseases including salmonellosis and *Salmonella* food poisoning caused by *Salmonella enteritidis* or *Salmonella typhimurium*, Fowl typhoid caused by *Salmonella gallinarum*, and Pullorum disease caused by *Salmonella* pullorum, which comprises the bacteriophage as an active ingredient, and an animal feed, drinking water, cleaner, and sanitizer which comprise the bacteriophage as an active ingredient.

8 Claims, 5 Drawing Sheets

SEQUENCE LISTING

<160> NUMBER OF SEQ ID NOS: 17

<210> SEQ ID NO 1
<211> LENGTH: 687
<212> TYPE: DNA
<213> ORGANISM: Bacteriophage KCCM11148P

<400> SEQUENCE: 1

```
acagctacgg gaccgcaggg cgcgttcctt aatctgcatt gtaagttccc ggccttcgtc    60
gctggcttcg gcacaggtaa atcggaagtc atgtgcaact ccgccctgtt agacagcatg   120
gaaggtggta gtgattcact tatcgtcttg tatgaaccga catacgacct ggtgcgcctt   180
atcctcgccc cgcgtatgga agaaaagttg tctgattggg gtattcgtta caagtacaat   240
aaatcaaaca acatagtcta tacatcatcc gggcaattcg gggattttgt cctgcgtaca   300
ttggataacc cggcgcgaat cgtgggttac gaatcttttc gcgcaaaaat agacgaattg   360
gacacgttaa ataaagacca ccccgagcac gcctggaaca aagctatcgc ccgtaaccgt   420
cagttgccgc gcacatatcg ttggaatacc ccaaagcctg ctaatacaga ttcggtattt   480
aatacacgtc acggcttctg ttttgtggtc catggatggg ttgacaaaaa gaatcgtggt   540
tgtgagatcc atcacgcccc gataacttct aaatcatttc taccggacga tcatgtccag   600
gctttgcgaa atacgaatcc tctttccttg aaatgtgctc tatctgtccg cgaatttgtt   660
gtcttaaagt ccggctacaa ttcatta                                        687
```

<210> SEQ ID NO 2
<211> LENGTH: 525
<212> TYPE: DNA
<213> ORGANISM: Bacteriophage KCCM11148P

<400> SEQUENCE: 2

```
tcggggtcca tgccaaacat cttacctgcg gttacgcagt aaatatccag cccggcgcgg    60
aacgtatcaa gcgcggtttc ttcgcccgcc agccatgcaa gcccacggcc ttcgacgtta   120
gagtaatccg caacaacaaa cttacgcccg gcttccggga taatgcagct tcggacggta   180
gacgctgtta gcttggccac atcaaaacgg cggtgtgcac ggcctttaag taacgcggca   240
atacccctat ccagttcatc gtcgtgataa tacccgcgcg ccaggttttg cggctgaaaa   300
cctttccccg cccaccgcat tgttcgcttc tctcctccgt attgccggca accacggcgg   360
cggtcatctg aaaaacggcc taacagcaac ggcgcgaatt tcttcaatgt ggaaaaaaca   420
accaccaccc gtctcactac aatagtgcgg acaaaaacaa gtaaatccac atccttcatc   480
aaatatttaa tgatgacttt tgtgcatttg tgaattcggt gcgct                   525
```

<210> SEQ ID NO 3
<211> LENGTH: 650
<212> TYPE: DNA
<213> ORGANISM: Bacteriophage KCCM11148P

<400> SEQUENCE: 3

```
acgcaaaccg tcgccgtaaa cgtccgcgtg gtaaacaaag cctgtatcag tcatccagac    60
attccgccga actatgggac ccggactatt gcgacgaatt aatccggttc ttcgaccgca   120
cgtcatggga actcgtaccc acgtctaaag gcgacgaacg cccgcttatc caggataaac   180
```

```
cgccatcact ggcccgtttc gcactacaca taggcgtaac cgttccgatt atcaagctgt      240
ggctgcgaga ggttcctgcc ttcgctgaag catacgaaac ggcgcaggcc ctggaagagg      300
cgtatttcac tgagaccggt gctgccggga tatctgctac gttcgccgca gcaaaacttg      360
ggcttaataa aactgttgtg gaagaagcgc gcgacgaacc aattagcgaa gtaactatta      420
aggtggtgtc cggtgaacgt tgatatcaca gctacgggac cgcagggcgc gttccttaat      480
ctgcattgta agttcccggc cttcgtcgct ggcttcggac caggtaaatc tgaacgaatg      540
cgcaaccccg ccctgctaca cagcgtggaa ggaggtagtg cttcccttct cttcgtctct      600
caacctacct attatctttt tcccctcccc tttttctccc ataatggacg                650
```

<210> SEQ ID NO 4
<211> LENGTH: 931
<212> TYPE: DNA
<213> ORGANISM: Bacteriophage KCCM11148P

<400> SEQUENCE: 4

```
actggcgact cacgcgcgta ggttctgtaa accgggtaac tatggttgtg ctgcgtgaga       60
catgggagta ccacgaacct ggaaacgagt tcgaaactaa atacggcgag cagtaccgcg      120
tgctggacat tgacaccgat ggtaattatc gtcagcgact gttccgtttc gatgcggaag      180
gcggagctca ggaagaggtt gtggagattt acccagattt aggggagtcg ttacgtggcg      240
taattccgtt taccttttatc ggagctacca ataacgacgc caccattgac gacgctcctt      300
tgttgccatt ggccgagctt aatatcgggc actaccggaa cagtgctgat aacgaggaat      360
caagttttgt agttggccag cctacgctgt ttatctaccc cggggataac cttacaccac      420
agtcgttcaa ggaagccaac cccaacggca tcaaatttgg cagtcggtgc gggcataacc      480
ttggttatgg tggtagcgct caacttattc aggcgggcga aaacaacctg gcccgccaga      540
atatgttgga caaagaacaa caggctatcc agattggcgc acagcttatt accccaaccc      600
agcaaattac cgcggaatcg gcgcgcatcc aacgcggcgc ggatacgtcc gttatgtcca      660
caatcgcccg taacgtaagt caggcgtata ctgatgcttt acgatgggtt gctatgatgt      720
tgggtaagcc agaagattct gaagtcgagt tccagcttat catggatttc ttcctgcaac      780
ctatgacagc acaggacagg gctgcgtgca tggcagacat taatgccgga ttactgcccg      840
ccactgctta ttacgctgcg ttgcgtaagg cgggggtgac tgactgaacc gacgaggata      900
ttctgaacgc tattgagatg cacctttgcc g                                    931
```

<210> SEQ ID NO 5
<211> LENGTH: 988
<212> TYPE: DNA
<213> ORGANISM: Bacteriophage KCCM11148P

<400> SEQUENCE: 5

```
gacaatgtgg gtgcttagcc gcctgtttcg caacgggcag ctaacagaag aagaccgggt       60
attaatcctc gccccgttgc gtgttgcgtc gggtacgtgg cccgcggaac aaactaagtg      120
ggggttccct tgccttcgtg tcatcgatgc aaccggttcg gagaagcgcc gcatagcggc      180
gctggagtcg gacgctaatg tggtgtgcac taactacgaa gttatcgagt ggctgattga      240
ttactacggc aaagacgact ggcctttttac tgttatcgtg gccgatgaga gcacgaaact      300
gaaatctttc cgcagccgtt caggcggtag caagcgggca aaggcgctta gtaaggtggc      360
gttcggtaaa gttaagcgtt tcattaacct gaccggtaca ccatcaccaa acggcctcaa      420
agacttgtgg ggtcagaact ggttcatcga cgcgggtgaa cgccttgggt cttcatacac      480
```

-continued

```
ggcctttacc gatagatggt ttaactcggt acagaaaggc aaatctgcga tggcgcggga    540
gtaccatgct cgcccaggcg cggataacga gattcaccag aagatgaagg atatcagcct    600
taccattgat gccgccgagt ggttcggttg tgaagcaccg gttattgtac cggttgagat    660
tgacctgccg aagaaagcgc gtcaagccta catcgatatg gaggaggagt tattcgcgga    720
actggagagc ggagaagttg aagcggctaa cgccgccgct aaaacggcta agtgcttgca    780
gattgcttcc ggtgccgtgt atgtgttcgg ggccggatgg tgaagcaacg aaagactggg    840
ataaagtgca ctacgctaaa cctcgatgct ttagagtcca ttgtcgagga gttgaaggtg    900
cgccgctgct ggttgaccta tctctttagc actaacttag aactgcagtc ctcaggcgca    960
tccctcttac gcagcagatc ctttcgcc                                       988
```

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
cgttccttaa tctgcattg                                                  19

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gctatggtga cgttgttg                                                   18

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
atgccaaaca tcttacc                                                    17

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gtattcgcag tagtgtcg                                                   18

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ggtaaacaaa gcctgtatc                                                  19

```
<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gattttgcac gtatctcg                                                   18

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gttcgaaact aaatacggc                                                  19

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gcgataaaag agtctatag                                                  19

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
cagctaacag aagaagac                                                   18

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
gatacgtttt atttctcgc                                                  19

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
gtaaaacgac ggccagt                                                    17

<210> SEQ ID NO 17
<211> LENGTH: 16
<212> TYPE: DNA
<213> ORGANISM: Artificial Sequence
```

```
<220> FEATURE:
<223> OTHER INFORMATION: Primer

<400> SEQUENCE: 17
aacagctatg accatg                                                    16
```

BACTERIOPHAGE OF THE SIPHOVIRIDAE FAMILY AND ANTIBACTERIAL COMPOSITIONS COMPRISING THE SAME

CROSS REFERENCE TO RELATED APPLICATIONS

This application claims benefit from U.S. provisional application Ser. No. 61/425,553 filed on Dec. 21, 2010, which are incorporated herein by reference in their entirety.

FIELD OF THE INVENTION

The present invention relates to a novel bacteriophage and antibacterial composition comprising the same.

BACKGROUND

*Salmonella* is a genus of the family Enterobacteriaceae, characterized as Gram-negative, facultatively anaerobic, non spore-forming, rod-shaped bacteria, and most strains are motile by flagella. *Salmonella* has an average genomic GC content of 50-52%, which is similar to that of *Escherichia coli* and *Shigella*. The genus *Salmonella* is a pathogenic microorganism that causes infections in livestock as well as in humans. Serological division has it that *Salmonella enterica*, a species of *Salmonella* bacterium, has a variety of serovars including *Gallinarum, Pullorum, Typhimurium, Enteritidis, Typhi, Choleraesuis,* and *derby* (Bopp C A, Brenner F W, Wells J G, Strokebine N A. *Escherichia, Shigella, Salmonella*. In Murry P R, Baron E J, et al., eds. *Manual of Clinical Microbiology*. 7th ed. Washington D.C. American Society for Microbiology 1999; 467-74; Ryan K J. Ray C G (editors) (2004). *Sherris Medical Microbiology* (4th ed). McGraw Hill. ISBN 0-8385-8529-9.). Of them, *Salmonella Gallinarum* and *Pullorum* are fowl-adapted pathogens, *Salmonella Typhi* is a human-adapted pathogen, *Salmonella Choleraesuis* and *Salmonella derby* are swine-adapted pathogens, and *Salmonella Enteritis* and *Salmonella Typhimurium* are pathogenic for humans and animals. Each serovar causes illness in the respective species, resulting in tremendous damage to farmers or consumers.

Meanwhile, *Salmonella Enteritidis* (hereinafter, referred to as "SE") and *Salmonella Typhimurium* (hereinafter, referred to as "ST") are zoonotic pathogens, which show no host specificity, unlike SG or SP (Zoobises Report; United Kingdom 2003).

SE and ST are causative of salmonellosis in poultry, pigs, and cattle. Salmonellosis, caused by *Salmonella* bacteria, is an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al., J. Anim. Sci. 86: E163-E172, 2008). In cattle, typical symptoms include loss of appetite, fever, dark brown diarrhea or bloody mucous in stool. The acute infection in calves leads to rapid death, and the infection during pregnancy leads to fetal death due to septicemia, resulting in premature abortion. In pigs, salmonellosis is characterized clinically by three major syndromes: acute septicemia, acute enteritis, and chronic enteritis. Acute septicemia occurs in 2-4 month-old piglets, and death usually occurs within 2-4 days after onset of symptoms. Acute enteritis occurs during the fattening period, and is accompanied by diarrhea, high fever, pneumonia, and nervous signs. Discoloration of the skin may occur in some severe case. Chronic enteritis is accompanied by continuing diarrhea.

Once an outbreak of salmonellosis by SE and ST occurs in poultry, pigs, and cattle, it is difficult to cure only with therapeutic agents. The reasons are that *Salmonella* bacteria exhibit a strong resistance to various drugs and live in cells that are impermeable to antibiotics upon the occurrence of clinical symptoms. Up to now, there have been no methods for effectively treating salmonellosis caused by SE and ST, including antibiotics.

As in livestock, SE and ST cause infections in humans via livestock and their products, leading to *salmonella* food poisoning. Intake of infected, improperly cooked livestock products (e.g., meat products, poultry products, eggs and by-products) infects humans. *Salmonella* food poisoning in humans usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. 2008. 01. 14.).

According to a report by the CDC (The Centers for Disease Control and Prevention, USA), 16% of human food poisoning outbreaks between 2005 and 2008 were attributed to *Salmonella* bacteria, with SE and ST responsible for 20% and 18% thereof, respectively. With respect to *Salmonella* food poisoning in humans between 1973 and 1984, the implicated food vehicles of transmission were reportedly chicken (5%), beef (19%), pork (7%), dairy products (6%), and turkey (9%). In 1974-1984, the bacterial contamination test on broilers during the slaughter process showed 35% or more of *Salmonella* incidence. In 1983, *Salmonella* was isolated in 50.6% of chicken, 68.8% of turkey, 60% of goose, 11.6% of pork, and 1.5% of beef. Further, a survey carried out in 2007 reported that *Salmonella* was found in 5.5% of raw poultry meat and 1.1% of raw pork. In particular, it was revealed that SE commonly originated from contaminated egg or poultry meat, and ST from contaminated pork, poultry meat, and beef Centers for Disease Control and Prevention (CDC)). For example, food poisoning caused by SE has rapidly increased in the US, Canada, and Europe since 1988, and epidemiological studies demonstrated that it was attributed to eggs or egg-containing foods (Agre-Food Safety Information Service (AGROS), Domestic and foreign food poisoning occurrence and management trend. February, 2008). A risk assessment conducted by FAO and WHO in 2002 noted that the human incidence of salmonellosis transmitted through eggs and poultry meat appeared to have a linear relationship to the observed *Salmonella* prevalence in poultry. This means that, when reducing the prevalence of *Salmonella* in poultry, the incidence of salmonellosis in humans will fall (*Salmonella* control at the source; World Health Organization, International Food Safety Authorities Network (INFOSAN) Information Note No. 03/2007). Recently, fears about food safety have been spurred by outbreaks of *Salmonella* from products as varied as peanuts, spinach, tomatoes, pistachios, peppers and, most recently, cookie dough (Jane Black and Ed O'Keefe, Overhaul of Food Safety Rules in the Works. Washington Post Staff Writers Wednesday, Jul. 8, 2009).

For these reasons, *Salmonella* infections must be reported in Germany (Sections 6 and 7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year (en.wikipedia.org/wiki/*Salmonella*#cite_note-2).

Therefore, there is an urgent need to control SE and ST, which cause salmonellosis in livestock and humans. The collaborative efforts of USDA and FDA have developed a number of effective strategies to prevent salmonellosis that causes over 1 million cases of food-borne illness in the United States. Among them is a final rule, issued by the FDA, to reduce the contamination in eggs. The FDA will now require that egg producers test regularly for lethal *salmonella* during egg production, storage and shipment. As a result, an estimated 79,000 illnesses and 30 deaths due to contaminated eggs will be avoided each year (Jane Black and Ed O'Keefe, Overhaul of Food Safety Rules in the Works. *Washington Post* Staff Writers Wednesday, Jul. 8, 2009). In Denmark, conservative estimates from a cost benefit analysis comparing *Salmonella* control costs in the production sector with the overall public health costs of salmonellosis suggest that *Salmonella* control measures saved Danish society US$ 14.1 million in the year 2001 (Salmonella control at the source, World Health Organization, International Food Safety Authorities Network (INFOSAN) Information Note No. 03/2007).

A disease of domestic birds caused by *Salmonella* bacterium is Fowl Typhoid (FT), which is caused by a pathogen, *Salmonella Gallinarum* (hereinafter, referred to as "SG"). Fowl Typhoid (FT) is a septicemic disease of domestic birds such as chicken and turkey, and the course may be acute or chronic with high mortality. A recent report has had it that Fowl Typhoid frequently occurs in Europe, South America, Africa, and Southeast Asia, with damages increasing every year. Outbreaks of FT in South Korea have been reported since 1992 and economic losses caused by FT in brown, egg-laying chickens are very serious (Kwon Yong-Kook, 2000 Annual Report on Avian Diseases, Information publication by National Veterinary Research & Quarantine Service. March, 2001; Kim Ae-Ran et al., The prevalence of pullorum disease-fowl typhoid in grandparent stock and parent stock in Korea, 2003, *Korean J. Vet. Res.* 46(4): 347-353, 2006).

Pullorum disease is also caused by a strain of the *Salmonella* bacteria, *Salmonella Pullorum* (hereinafter, referred to as "SP"). Pullorum disease occurs in any age or season, but young chickens are particularly susceptible to the disease. During the past century, it has been a serious disease among young chickens at 1-2 weeks of age or younger. Since the 1980s, the occurrence has greatly decreased. However, it has been growing since the mid-1990s (Kwon Yong-Kook, 2000 Annual Report on Avian Diseases, Information publication by National Veterinary Research & Quarantine Service. March, 2001; Kim Ae-Ran et al., The prevalence of pullorum disease-fowl typhoid in grandparent stock and parent stock in Korea, 2003, *Korean J. Vet. Res.* 46(4): 347-353, 2006).

In South Korea, outbreaks of Fowl Typhoid and Pullorum disease have been increasing since the 1990s, inflicting economic damages on farmers. For this reason, a live attenuated SG vaccine has been used in broilers for the prevention of Fowl Typhoid from 2004 (Kim Ae-Ran et al., The prevalence of pullorum disease-fowl typhoid in grandparent stock and parent stock in Korea, 2003, *Korean J. Vet. Res.* 46(4): 347-353, 2006). Its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

Meanwhile, bacteriophage is a specialized type of virus that infects and destroys only bacteria, and can self-replicate only inside host bacteria. Bacteriophage consists of genetic material in the form of single or double stranded DNA or RNA surrounded by a protein shell. Bacteriophages are classified based on their morphological structure and genetic material. There are three basic structural forms of bacteriophage according to morphological structure: an icosahedral (twenty-sided) head with a tail; an icosahedral head without a tail; and a filamentous form. Based on their tail structure, bacteriophages having icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having an icosahedral head without a tail and RNA or DNA as their genetic material are divided based on their head shape and components, and the presence of shell. Filamentous bacteriophages having DNA as their genetic material are divided based on their size, shape, shell, and filament components (H. W. Ackermann. Frequency of morphological phage descriptions in the year 2000; *Arch. Virol.*, 146: 843-857, 2001; Elizabeth Kutter et al., Bacteriophages Biology and Application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle.

After the discovery of bacteriophages, a great deal of faith was initially placed in their use for infectious-disease therapy. However, when broad spectrum antibiotics came into common use, bacteriophages were seen as unnecessary due to a specific target spectrum. Nevertheless, the misuse and overuse of antibiotics resulted in rising concerns about antibiotic resistance and harmful effects of residual antibiotics in foods. In particular, antimicrobial growth promoter (AGP), added to animal feed to enhance growth, is known to induce antibiotic resistance, and therefore, the ban of using AGP has been recently introduced. In the European Union, the use of all AGPs was banned from 2006. South Korea has banned the use of some AGPs from 2009, and is considering restrictions on the use of all AGPs in 2013~2015.

These growing concerns about the use of antibiotics have led to a resurgence of interest in bacteriophage as an alternative to antibiotics. Seven bacteriophages for control of *E. coli* O157:H are disclosed in U.S. Pat. No. 6,485,902 (Use of bacteriophages for control of *Escherichia coli* O157, issued in 2002). Two bacteriophages for control of various microorganisms are disclosed in U.S. Pat. No. 6,942,858 (issued to Nymox in 2005). Many companies have been actively trying to develop various products using bacteriophages. EBI Food System (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally Regarded As Safe). In 2007, a phage-based wash produced by OmniLytics was developed to prevent *E. coli* O157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli, Listeria,* and *Clostridium. Salmonella* is also a zoonotic pathogen, and damages due to this pathogen are not reduced. As mentioned above, since SE and ST exhibit multiple drug resistance, nationwide antimicrobial resistance surveillance has been conducted in South Korea under the Enforcement Decree of the Act on the Prevention of Contagious Disease (Executive Order 16961), Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella.*

In order to solve the problems including antibiotic resistance due to the misuse and overuse of antibiotics, harmful effects of residual antibiotics in foods, and the problems generated by the use of broad spectrum antibiotics, the present inventors isolated from natural sources a novel bacteriophage having a specific bactericidal activity against *Salmonella* which causes major diseases in livestock, and identified its morphological, biochemical, and genetic properties. The present inventors found that the bacteriophage has a specific bactericidal activity against *Salmonella entieritidis, Salmonella typhimurium, Salmonella gallinarum* and *Salmonella pullorum* without affecting beneficial bacteria, and excellent acid-, heat- and dry-resistance, and thus can be applied to the compositions that can be used for the prevention or treatment of livestock salmonellosis caused by *Salmonella entieritidis* or *Salmonella typhimurium, Salmonella* food poisoning caused by contaminated livestock products, and infectious diseases caused by *Salmonella gallinarum* or *Salmonella pullorum,* in particular, Fowl typhoid or Pullorum disease, and to various products to control *Salmonella,* such as animal feed additive and drinking water for livestock, barn sanitizers, and cleaners for meat products, thereby completing the present invention.

SUMMARY OF THE INVENTION

It is an object of the present invention to provide a novel bacteriophage which has a specific bactericidal activity against one or more *Salmonella* bacteria selected from the group consisting of *Salmonella Enteritidis, Salmonella Typhimurium, Salmonella Gallinarum,* and *Salmonella Pullorum.*

It is another object of the present invention to provide a composition for the prevention or treatment of infectious diseases caused by one or more *Salmonella* bacteria selected from the group consisting of *Salmonella Enteritidis, Salmonella Typhimurium, Salmonella Gallinarum,* and *Salmonella Pullorum,* comprising the bacteriophage as an active ingredient.

It is still another object of the present invention to provide an animal feed and drinking water, comprising the bacteriophage as an active ingredient.

It is still another object of the present invention to provide a sanitizer and cleaner, comprising the bacteriophage as an active ingredient.

It is still another object of the present invention to provide a method for preventing or treating livestock salmonellosis or *Salmonella* food poisoning caused by *Salmonella Enteritidis* or *Salmonella typhimurium,* using the composition that comprises the bacteriophage as an active ingredient.

It is still another object of the present invention to provide a method for preventing or treating infectious diseases, Fowl Typhoid or Pullorum disease caused by *Salmonella gallinarum* or *Salmonella pullorum.*

■: male control group administered with the mixed solution of 20 mM Tris-HCl and 2 mM MgCl$_2$;

□: male test group administered with ΦCJ8 at a concentration of 1×10$^{12}$ pfu;

●: female control group administered with the mixed solution of 20 mM Tris-HCl and 2 mM MgCl$_2$; and ○: female test group administered with ΦCJ8 at a concentration of 1×10$^{12}$ pfu.

DETAILED DESCRIPTION OF THE INVENTION

In accordance with an aspect, the present invention relates to a novel bacteriophage having a specific bactericidal activity against *Salmonella entieritidis* (SE), *Salmonella typhimurium* (ST), *Salmonella gallinarum* (SG) or *Salmonella pullorum* (SP).

Figure 1:
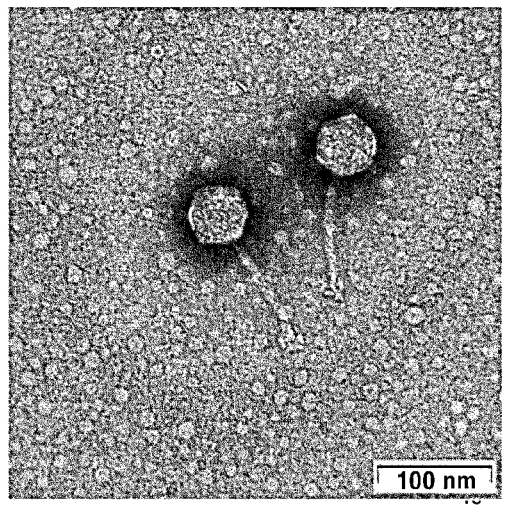
FIG. 1 is an electron microphotograph of ΦCJ8, showing that ΦCJ8 belongs to a morphotype group of the family Siphoviridae, characterized by an isometric capsid and a long non-contractile tail.
Figure 2:
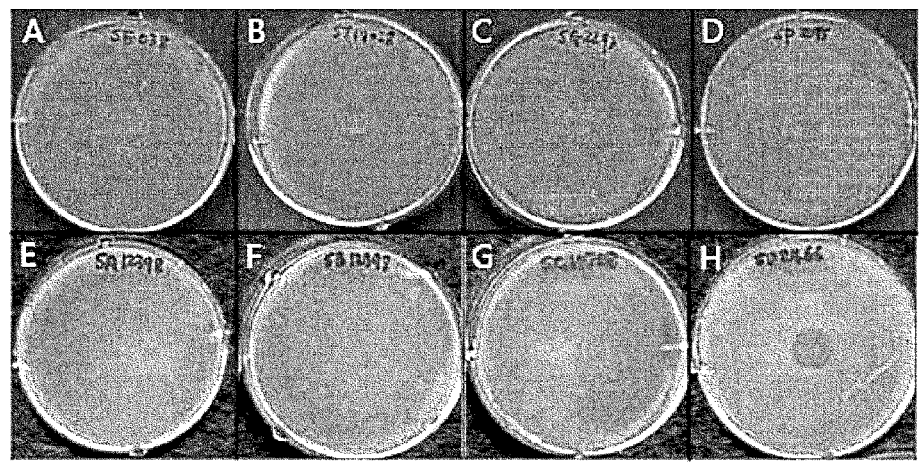
FIG. 2 is of photographs showing the formation of ΦCJ8 plaques in a lawn of *salmonella* bacteria. ΦCJ8 plaques formed in lawns of SE, ST, SG and SP, but not in, lawns of SA, SB, SC and SD.
A: in a lawn of SE;
B: in a lawn of ST;
C: in a lawn of SG;
D: in a lawn of SP;
E: in a lawn of SA;
F: in a lawn of SB;
G: in a lawn of SC; and
H: in a lawn of SD

The present inventors collected sewage samples at chicken slaughterhouses, and isolated therefrom a bacteriophage having a specific bactericidal activity against SE, ST, SG and SP (see FIG. 2 and Table 1). As a result of morphological examination under an electron microscope, the bacteriophage of the present invention belongs to the morphotype of the family Siphoviridae, characterized by an isometric capsid and a long non-contractile tail (see FIG. 1).

Figure 3:
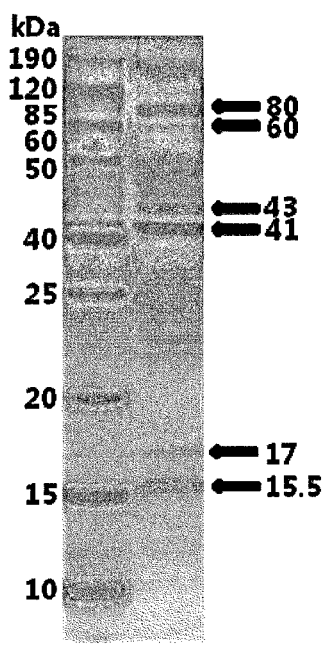
FIG. 3 is the result of SDS-PAGE of the isolated bacteriophage ΦCJ8, in which protein patterns of the bacteriophage are shown, including major proteins of 41, 80, 15.5, 60 and 43 kDa (here, unstained BenchMark Protein ladder (Invitrogen) used as a size marker).

The bacteriophage of the present invention includes major structural proteins with size of approximately 41, 80, 15.5, 60 and 43 kDa, as measured by a protein pattern analysis (see FIG. 3).

Further, the bacteriophage of the present invention genetically has a total genome size of approximately 44.1 to 49 kbp (see FIG. 4), and may include one or more nucleic acid molecules selected from the group consisting of SEQ ID NOs: 1 to 5 within the entire genome. Also, as a result of comparing genetic similarity with other species based on the above nucleotide sequences, since there is very low genetic similarity between the bacteriophage of the present invention and the known bacteriophages, the bacteriophage of the present invention is novel (see Table 2). More particularly, when the bacteriophage of the present invention is subjected to PCR using one or more primer sets selected from the group consisting of SEQ ID NOs: 6 and 7, SEQ ID NOs: 8 and 9, SEQ ID NOs: 10 and 11, SEQ ID NOs: 12 and 13, and SEQ ID NOs: 14 and 15, the resulting PCR products are approximately 3.5, 2.1, 1.6, 1.2 and 1.4 kbp in size, respectively (see FIG. 5).

Also, the phage plaques (clear zones formed in a lawn of cells on soft agar due to lysis by phage) resulting from the infection of the bacteriophage according to the present invention into SE, ST, SG and SP were observed to have the same size and turbidity (see FIG. 2).

The bacteriophage of the present invention has the biochemical properties of acid- and heat-resistance. As a result of examining stability under a wide spectrum of pH and temperature, the bacteriophage of the present invention can survive over a pH range of from 3.0 to 11.0 (see FIG. 6) and a temperature range of from 37 to 70° C. (see FIG. 7). Further, the bacteriophage of the present invention has dry-resistance to stably maintain its activity even after desiccation at high temperature (see FIG. 8). Such properties of acid-, heat-, and drying-resistance allow application of the bacteriophage of the present invention under various temperature and pH conditions upon the production of prophylactic or therapeutic compositions for livestock diseases caused by SE, ST, SG and SP or human diseases caused by the contaminated livestock.

Also, the bacteriophage of the present invention can infect wild-type strains SE, ST, SG and SP (see Table 3).

Figure 9:
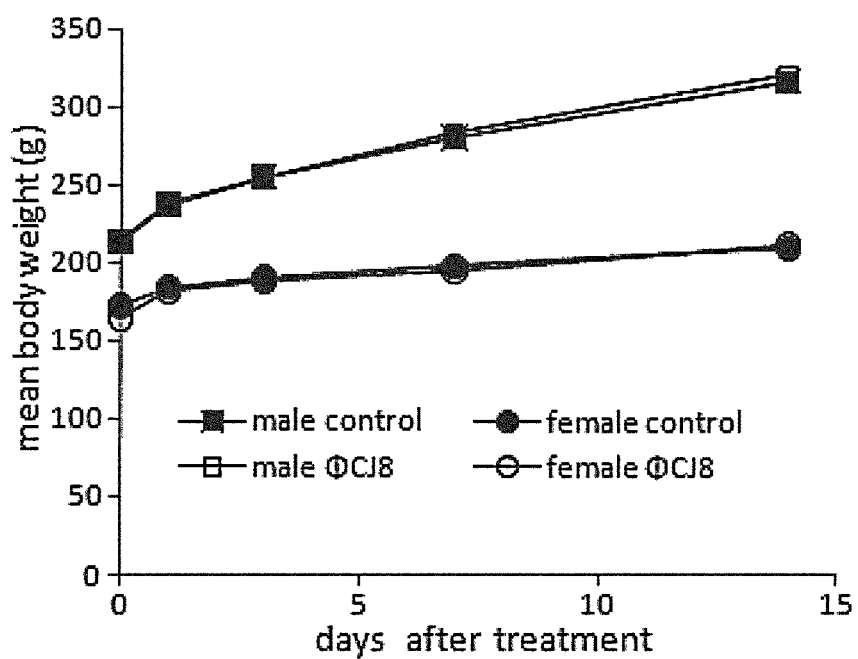
FIG. 9 is a graph in which body weights of rats are plotted against time after administration with single dose of the bacteriophage ΦCJ8. No significant change in body weight was found even 14 days after the administration, as compared to the control.

When the bacteriophage of the present invention is orally administered to rats, there is no change in body weight, mortality, general symptoms and organ abnormality (see FIG. 9, Tables 4 and 5).

Also, when the bacteriophage of the present invention is used as a feed additive of broilers, it does not show any negative effect on growth performance or development of organs and muscles in broilers (see Tables 6 and 7).

The results of testing the efficacy, sanitizing effect and cleaning efficiency showed that when used in livestock farms, the bacteriophage of the present invention can effectively control *Salmonella* (SE) by inhibiting its propagation and fecal shedding (see Tables 8 and 9), and has excellent and consistent bactericidal activity against *Salmonella* under various conditions, compared to conventional cleaners as a positive control.

These data imply that the bacteriophage of the present invention can be applied to various products for the control of *Salmonella* bacteria.

The bacteriophage of the present invention having a specific bactericidal activity against SE, ST, SG and SP and the above characteristics has been designated as ΦCJ8 and deposited with the Korean Culture Center of Microorganisms (361-221, Honje 1-dong, Seodaemun-gu, Seoul, South Korea) on Dec. 14, 2010 under accession number KCCM11148P.

In accordance with another aspect, the present invention pertains to a composition for the prevention or treatment of infectious diseases caused by one or more *Salmonella* bacteria selected from the group consisting of *Salmonella enteritidis, Salmonella typhimurium, Salmonella gallinarum* and *Salmonella pullorum*, comprising the bacteriophage as an active ingredient.

Having a specific bactericidal activity against *Salmonella enteritidis, Salmonella Typhimurium, Salmonella Gallinarum* and *Salmonella Pullorum*, the bacteriophage of the present invention can be used for preventing or treating diseases caused thereby. In a preferred embodiment, the composition of the present invention may further comprise an antibiotic.

Preferably, examples of the infectious diseases include salmonellosis and *Salmonella* food poisoning by *Salmonella enteritidis* or *Salmonella Typhimurium*, Fowl Typhoid by *Salmonella Gallinarum* and Pullorum disease by *Salmonella Pullorum*, but are not limited thereto.

As used herein, the term "salmonellosis" refers to symptoms following *salmonella* infection, such as fever, headache, diarrhea, and vomiting. That is, salmonellosis is an infection with bacteria of the genus *Salmonella*, with the accompaniment of two representative symptoms: septicemia such as typhoid fever; and acute gastroenteritis such as food poisoning, enteritis, and acute bacteremia.

As used herein, the term "prevention" is intended to encompass all actions for restraining or delaying disease progress through the administration of the composition. The term "treatment" in this context encompasses all actions for improving or beneficially changing the patient's condition through the administration of the composition.

The composition of the present invention comprises the bacteriophage of the present invention as an active ingredient in an amount of from 5×10$^2$ to 5×10$^{12}$ pfu/Ml, and preferably in an amount of from 1×10$^6$ to 1×10$^{10}$ pfu/Ml.

The composition of the present invention may further comprise a pharmaceutically acceptable vehicle, and may be formulated together with the carrier into foods, medicines, and feed additives.

As used herein, the term "pharmaceutically acceptable vehicle" refers to a carrier or diluent that neither causes significant irritation to an organism nor degrades the biological activity and properties of the administered active ingredient. For use in the formulation of the composition into a liquid preparation, a pharmaceutically acceptable vehicle must be suitable for sterilization and biocompatibility. Examples include saline, sterile water, Ringer's solution, buffered physiological saline, albumin infusion solution, dextrose solution, maltodextrin solution, glycerol, and ethanol. They may be used alone or in any combination thereof. If necessary, another conventional additive, such as antioxidants, buffers, bacteriostatic agents, etc., may be added to the composition. When combined additionally with diluents, dispersants, surfactants, binders and/and lubricants, the composition of the present invention may be formulated into injections such as aqueous solutions, suspensions and emulsions, or pills, capsules, granules, or tablets.

The prophylactic or therapeutic compositions of the present invention may be locally applied to afflicted areas by coating or spraying. Alternatively, the composition of the present invention may be administered through oral or parenteral routes. The parenteral routes are available for intravenous, intraperitoneal, intramuscular, subcutaneous or topical administration Depending on a variety of factors including formulations, the mode of administration, the age, weight, sex, condition and diet of the patient or animal being treated, the time of administration, the route of administration, the rate of excretion, and reaction sensitivity, the suitable dosage of the composition of the present invention will vary when it is applied, sprayed or administered. It will be apparent to those skilled in the art that when the pharmaceutical composition is administered to patients, the suitable total daily dose may be determined by an attending physician or veterinarian within the scope of sound medical judgment.

Oral dosage preparations of the composition of the present invention may take the form of tablets, troches, lozenges, aqueous or emulsive suspensions, powders or granules, emulsions, hard or soft capsules, syrups, or elixirs. The oral dosage forms such as tablets and capsules may comprise a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid vehicle such as lipid may be further used.

For non-oral administration, the composition of the present invention may be formulated into injections via subcutaneous, intravenous, or intramuscular routes, suppositories, or sprays inhalable via the respiratory tract, such as aerosols. Injection forms may be prepared by dissolving or suspending the composition of the present invention, together with a stabilizer or a buffer, in water and loading the solution or suspension onto ampules or vial unit forms. For sprays, such as aerosols, a propellant for spraying a water-dispersed concentrate or wetting powder may be used in combination with an additive.

The term "antibiotic", as used herein, refer to a substance or compound that can be administered to animals to kill bacteria or inhibit their growth and is intended to encompass antiseptics, bactericidal agents and antibacterial agents. The animals are mammals including humans. Thanks to the advantage of being of higher specificity for *Salmonella* over conventional antibiotics, the bacteriophage of the present invention can kill the specific pathogens without affecting beneficial bacteria. Furthermore, the bacteriophage of the present invention does not induce drug resistance so that it can be provided as a novel antibiotic with a long life cycle.

In accordance with a further aspect, the present invention relates to an animal feed or drinking water, comprising the bacteriophage as an active ingredient.

Feed additive antibiotics used in the fishery and livestock industry are intended to prevent infections. However, most of the currently available feed additive antibiotics are problematic in that they are apt to induce the occurrence of resistant strains and may be transferred to humans as they remain in livestock products. The uptake of such residual antibiotics may make human pathogens resistant to antibiotics, resulting in the spread of diseases. Furthermore, many kinds of feed additive antibiotics, usually used in combination in animal feeds, may cause the emergence of multidrug-resistant strains. Therefore, the bacteriophage of the present invention can be used as a feed additive antibiotic that is eco-friendly enough to be a solution to the problems.

The animal feed according to the present invention may be prepared by adding the bacteriophage directly or in a separate feed additive form to an animal feed. In an animal feed, the bacteriophage of the present invention may take a liquid or a dry form, and preferably exist as a dried powder. In this regard, the bacteriophage of the present invention may be dried by air drying, natural drying, spray drying or freeze-drying, but these drying processes do not limit the present invention. The bacteriophage of the present invention may be added as powder in an amount of from 0.05 to 10% by weight, preferably in an amount of from 0.1 to 2% by weight, based on the total weight of animal feed. The animal feed may comprise other conventional additives useful for the preservation thereof for a long term, in addition to the bacteriophage of the present invention.

To the feed additive of the present invention may be added another non-pathogenic microorganism. The available additional microorganism may be selected from the group consisting of *Bacillus subtilis* that can produce protease, lipase and invertase, *Lactobacillus* sp. strain that can exert physiological activity and a function of decomposing under an aerobic conditions, such as in the stomach of cattle, filamentous fungi including *Aspergillus oryzae* (J. Animal. Sci. 43: 910-926, 1976) that increases the weight of domestic animals, enhances milk production and helps the digestion and absorptiveness of feeds, and yeast including *Saccharomyces cerevisiae* (J. Anim. Sci. 56: 735-739, 1983).

The animal feed comprising the bacteriophage of the present invention may include plant-based feeds, such as grains, nuts, food byproducts, seaweed, fiber, drug byproducts, oil, starches, meal, and grain byproducts, and animal-based feeds such as proteins, minerals, fat, single cell proteins, zooplankton, and food wastes, but is not limited thereto.

The feed additive comprising the bacteriophage of the present invention may include additives for preventing quality deterioration, such as binders, emulsifiers and preservatives, and additives for increasing utility, such as amino acids, vitamins, enzymes, probiotics, flavorings, non-protein nitrogen, silicates, buffering agents, coloring agents, extracts, and oligosaccharides, but is not limited thereto.

When supplied with drinking water containing the bacteriophage of the present invention, livestock can be continuously reduced in the population of *Salmonella* bacteria in the intestine thereof livestock. As a result, *Salmonella*-free livestock can be produced.

In accordance with still further aspect, the present invention pertains to a cleaner or a sanitizer, comprising the bacteriophage as an active ingredient.

The sanitizer comprising the bacteriophage of the present invention as an active ingredient is very useful for food hygiene against, for example, food poisoning. In detail, the sanitizer may be utilized not only as an agent or a food additive for preventing *salmonella* contamination, but also in the production of *Salmonella*-free livestock. In order to remove *Salmonella*, the sanitizer can also be sprayed over domestic sewages and applied to poultry barns, slaughterhouses, spots where livestock died, cooking spaces and cooking facilities.

Further, the cleaner comprising the bacteriophage of the present invention as an active ingredient can be used on a body area of living animals, such as skin, feathers and the like, which is already or potentially contaminated with *Salmonella* bacteria.

In accordance with still another aspect, the present invention relates to a method for the prevention or treatment of infectious diseases caused by one or more *Salmonella* bacteria selected from the group consisting of *Salmonella enteritidis, Salmonella typhimurium, Salmonella gallinarum* and *Salmonella pullorum* using the bacteriophage or the composition comprising the same.

The composition of the present invention may be administered in the form of a pharmaceutical formulation into animals or may be ingested as a mixture with animal feed or drinking water by animals and preferably as a mixture with animal feed. In the present invention, the animals include cattle, pigs, chicken, poultry and humans, but are not limited thereto.

As long as it reaches target tissues, any route, whether oral or parenteral, may be taken for administering the composition of the present invention. In detail, the composition of the present invention may be administered via oral, rectal, topical, intravenous, intraperitoneal, intramuscular, intraarterial, transdermal, intranasal, and inhalation routes.

The method for the treatment of diseases in accordance with the present invention comprises administering the composition of the present invention in a therapeutically effective amount. It is apparent to those skilled in the art that the total daily dose should be determined by an attending physician or veterinarian within the scope of sound medical judgment. The therapeutically effective amount for a given patient may vary depending on various factors well known in the medical art, including the kind and degree of the response to be achieved, the patient's age, body weight, state of health, sex, and diet, time and route of administration, the secretion rate of the composition, the time period of therapy, concrete compositions according to whether other agents are used therewith or not, etc.

As described above, the novel bacteriophage of the present invention has a specific bactericidal activity against *Salmonella entieritidis, Salmonella typhimurium, Salmonella gallinarum* and *Salmonella pullorum*, and excellent acid-, heat- and dry-resistance. Thus, it can be used for the prevention or treatment of infectious diseases caused by *Salmonella entieritidis, Salmonella typhimurium, Salmonella gallinarum* and *Salmonella pullorum*, including salmonellosis, *Salmonella* food poisoning, Fowl typhoid or Pullorum disease, and also used for the control of *Salmonella entieritidis, Salmonella typhimurium, Salmonella gallinarum* and *Salmonella pullorum*.

A better understanding of the present invention may be obtained through the following examples which are set forth to illustrate, but are not to be construed as limiting the present invention.

EXAMPLE 1

Salmonella Bacteriophage Isolation 1-1. Bacteriophage Screening and Single Bacteriophage Isolation 50 Ml of each sample from a chicken slaughterhouse, located in Muan, Jeollanam-do, South Korea, and a nearby sewage disposal plant were transferred to a centrifuge tube, and centrifuged at 4000 rpm for 10 min, followed by filtering the supernatant through a 0.45 μm filter. 18 Ml of the sample filtrate was mixed with 150 μl of a *Salmonella enteritidis* (hereinafter referred to as "SE") shaking culture medium ($OD_{600}$=2) and 2 Ml of 10× Luria-Bertani (LB) medium (tryptone 10 g; yeast extract 5 g; NaCl 10 g; in a final volume of 1 l). The mixture was cultured at 37° C. for 18 hrs and then centrifuged at 4000 rpm for 10 min after which the supernatant was filtered through a 0.45 μm filter. Separately, a mixture of 3 Ml of 0.7% agar (w/v) and 150 μl of the SE shaking culture medium ($OD_{600}$=2) was poured across an LB plate and allowed to solidify. Over this plate was spread 10 μl of the culture filtrate, followed by incubation for 18 hrs at 37° C. (0.7% agar was used as "top-agar" and the titration of phage lysate was performed on the top-agar, called soft agar overlay technique).

The sample culture medium containing the phage lysate was appropriately diluted, mixed with 150 μl of an SSE shaking culture solution ($OD_{600}$=2), and then, subjected to soft agar overlay assay to produce a single plaque. Since a single plaque consisted of one bacteriophage, one plaque was taken and dissolved in 400 μl of an SM solution (NaCl, 5.8 g; $MgSO_4 \cdot 7H_2O$, 2 g; 1 M Tris-HCl (pH 7.5), 50 Ml; $H_2O$, in a final volume of 1 l), and left for 4 hours at room temperature to isolate a single bacteriophage. To amplify the isolated bacteriophage, 100 μl of the supernatant was taken from the single bacteriophage solution, mixed with 5 Ml of 0.7% agar and 100 μl of an SE shaking culture solution, and subjected to a soft agar overlay assay on an LB plate (90 mm in diameter). 5 Ml of the SM solution was poured to a plate in which lysis had been completed, after which the plate was gently shaken for 4 hrs at room temperature to elute the bacteriophages from the top-agar. The SM solution containing the eluted bacteriophages was recovered, and chloroform was added thereto in an amount corresponding to 1% of the final volume, and mixed well for 10 min. After centrifugation at 4000 rpm for 10 minutes, the resulting supernatant was filtered through a 0.45 μm filter, and stored in the refrigerator until use.

1-2. Large-Scale Culture of Bacteriophage

The selected bacteriophage was cultured at a large scale using SE. SE was cultured with shaking. After an aliquot of $1.5 \times 10^{10}$ cfu (colony forming units) was centrifuged at 4000 rpm for 10 min, the pellet was re-suspended in 4 Ml of the SM solution. Into the suspension was inoculated $1.5 \times 10^6$ pfu (plaque forming unit) of the bacteriophage at an MOI (multiplicity of infection) of 0.0001, followed by incubation at 37° C. for 20 min. This solution was inoculated into 150 Ml of the LB media in a flask, and cultured at 37° C. for 5 hrs. Chloroform was added thereto in an amount corresponding to 1% of the final volume before the culture solution was shaken for 20 min. DNase I and RNase A were added to a final concentration of 1 μg/Ml, respectively. The solution was left at 37° C. for 30 min. NaCl and PEG (polyethylene glycol) were added thereto at a final concentration of 1 M and 10% (w/v), respectively, and left at 4° C. for further 3 hrs. The solution was centrifuged at 4° C. and 12,000 rpm for 20 min to discard the supernatant. Thus obtained pellet was resuspended in 5 Ml of the SM solution, and left at room temperature for 20 minutes. To the suspension, 4 Ml of chloroform was added and mixed well. After centrifugation at 4° C., 4000 rpm for 20 min, the supernatant was filtered through a 0.45 μm filter and then subjected to ultracentrifugation using a glycerol density gradient to purify a bacteriophage (density: 40%, 5% glycerol at 35,000 rpm and 4° C. for 1 hr). The purified bacteriophage was designated as ΦCJ8. The bacteriophage ΦCJ8 was resuspended in 300 μl of the SM solution, followed by titration. The bacteriophage ΦCJ8 was deposited with the Korean Culture Center of Microorganisms (361-221, Honje 1-dong, Seodaemun-gu, Seoul, South Korea) on Dec. 14, 2010 under accession number KCCM1100148P.

EXAMPLE 2

Examination on ΦCJ8 Infection to Salmonella

To analyze the selected bacteriophage for lytic activity on *Salmonella* species other than SE, attempts were made of cross infection with other *Salmonella* species. As a result, ΦCJ8 did not infect SC (*Salmonella choleraesuis*), SD (*Salmonella derby*), SA (*Salmonella arizonae*) and SB (*Salmonella bongori*), but infected SE (*Salmonella enteritidis*), ST (*Salmonella typhimurium*), SG (*Salmonella gallinarum*) and SP (*Salmonella pullorum*). The results are, summarized in Table 1 and shown in FIG. 1.

TABLE 1

ΦCJ8 Infection to *Salmonella*

| Sero type | Strain name | Plaque formation | Sero type | Strain name | Plaque formation |
|---|---|---|---|---|---|
| SE | SGSC 038 | ○ | SA | ATCC 12398 | X |
| ST | SGSC 14028 | ○ | SB | ATCC 12397 | X |
| SG | SGSC 2293 | ○ | SC | ATCC 10708 | X |
| SP | SGSC 2295 | ○ | SD | ATCC 2466 | ○ |

* ATCC: The Global Bioresource Center
* SGSC: Salmonella Genetic Stock Center

EXAMPLE 3

Morphological Analysis of ΦCJ8

The purified ΦCJ8 was diluted in a 0.01% gelatin solution, and then fixed in a 2.5% glutaraldehyde solution. The sample was dropped onto a carbon-coated mica plate (ca. 2.5×2.5 mm), adapted for 10 min, and washed with sterile distilled water. A carbon film was mounted on a copper grid, stained with 2% uranyl acetate for 3-5 sec, and dried. Examination under a transmission electron microscope (LIBRA 120, Carl Zeiss transmission electron microscope, 80 kV, magnification of ×120,000 to ×200,000) showed that the purified ΦCJ8 consisted morphologically of an isometric capsid and a long non-contractile tail, indicating that it belongs to a morphotype group of the family Siphoviridae.

EXAMPLE 4

Protein Pattern Analysis of ΦCJ8

15 μl of a ΦCJ8 solution purified at a titer of $10^{12}$ pfu/Ml was mixed with 3 μl of a 5×SDS sample solution, and heated for 5 min. The total protein of ΦCJ8 was run on 15% SDS-PAGE gel. Then, the gel was stained with Coomassie blue for 1 hr at room temperature. Major bands were detected at approximately 41, 80, 15.5, 60 and 43 kDa, as shown in FIG. 3.

EXAMPLE 5

Total Genomic DNA Size of ΦCJ8

Figure 4:
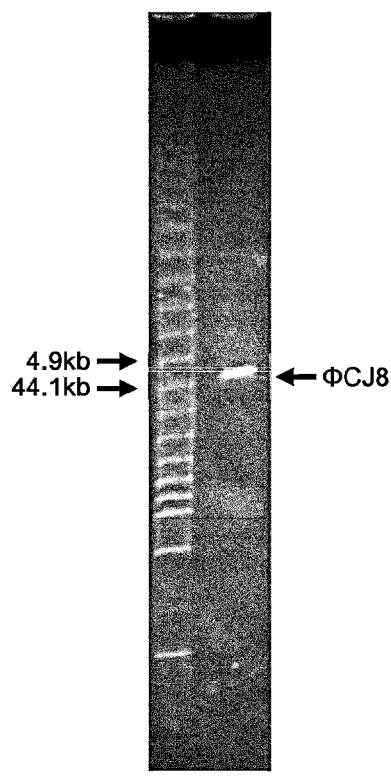
FIG. 4 is the result of PFGE of the isolated bacteriophage ΦCJ8, showing the total genome size of approximately 44.1 to 49 kbp (here, 5 kbp CHEF DNA size standard (BIO-RAD) used as a size marker).

Genomic DNA of ΦCJ8 was isolated using ultracentrifugation. In particular, to a purified ΦCJ8 culture solution were added EDTA (ethylene diamine tetraacetic acid, pH 8.0), proteinase K, and SDS (sodium dodecyl sulfate) at a final concentration of 20 mM, 50 μg/Ml, and 0.5% (w/v), respectively, followed by incubation at 50° C. for 1 hr. An equal volume of phenol (pH 8.0) was added and mixed well. After centrifugation at 12,000 rpm and room temperature for 10 min, the supernatant was mixed well with an equal volume of PC (phenol:chloroform=1:1). Another centrifugation at 12,000 rpm and room temperature for 10 min produced a supernatant, which was then mixed with 1/10 volume of 3 M sodium acetate and two volumes of cold 95% ethanol, and left at −20° C. for 1 hr. After that, the resulting mixture was subjected to centrifugation at 0° C., 12,000 rpm for 10 min, to thereby completely remove a supernatant. The resulting DNA pellet was dissolved in 50 μl of TE (Tris-EDTA, pH 8.0). The extracted DNA was diluted 10-fold, and measured for absorbance at $OD_{260}$ to determine its concentration. 1 μg of the total genomic DNA was loaded onto 1% PFGE (pulse-field gel electrophoresis) agarose gel and electrophoresed at room temperature for 20 hrs with the aid of a BIORAD PFGE system program 7 (size range 25-100 kbp; switch time ramp 0.4-2.0 seconds, linear shape; forward voltage 180 V; reverse voltage 120 V). As shown in FIG. 4, the genomic DNA of ΦCJ8 was in the range of approximately 44.1 to 49 kbp long.

EXAMPLE 6

Genetic Analysis of ΦCJ8

The genetic analysis of the purified ΦCJ8 started with simultaneously digesting 5 of the genomic DNA of ΦCJ8 with three combinations of restriction enzymes: SaII and XhoI, EcoRV and NruI, HinCII and PvuII. Separately, a pBluscript H SK(+) vector was digested with EcoRV, and treated with CIP (calf intestinal alkaline phosphatase). The digested genomic DNA was mixed at a ratio of 3:1 with the vector, and ligated at 16° C. for 2 hrs. The resulting recombinant vector was transformed into *E. coli* DH5α, which was then plated on an LB plate containing ampicillin and X-gal (5-bromo-4-chloro-3-indolyl-beta-D-galactopyranoside) for blue/white colony selection. The selected colonies were cultured for 16 hrs in the LB medium containing ampicillin with shaking. Then, plasmids were extracted using a plasmid purification kit (Promega).

The cloning of the plasmid was confirmed by PCR using a primer set of M13 forward and reverse (SEQ ID NOs: 16 and 17), and selection was made only of insert fragments having a size of 1 kb or longer. Thus selected plasmids were subjected to sequence analysis using the above primer set. The base sequences thus obtained were given in SEQ ID NOs: 1 to 5, each being approximately 1 to 4 kb in size, and analyzed for sequence similarity with the aid of NCBI blastx and blastn programs. The results are summarized in Table 2.

TABLE 2

Sequence Similarity between ΦCJ8 and Other Bacteriophages

| | | | Blastx | | | |
|---|---|---|---|---|---|---|
| No | Organism | Protein | Query | Subject | Identity | e-value |
| 1 | Salmonella phage SETP3 | hypothetical protein | 1-672 | 6-516 | 183/224 (81%) | 1e-97 |
| | Salmonella phage KS7 | hypothetical protein | 1-675 | 6-230 | 181/225 (80%) | 3e-96 |
| | Salmonella phage KS7 | structural protein | 651-211 | 345-491 | 116/147 (78%) | 2e-57 |
| | Salmonella phage SETP3 | putative structural protein | 651-235 | 345-481 | 92/139 (66%) | 1e-47 |
| | Salmonella phage SETP3 | amidase | 1-171 | 159-215 | 55/57 (96%) | 6e-24 |
| | Salmonella phage E1 | hypothetical protein | 1-171 | 160-216 | 53/57 (92%) | 1e-22 |
| 2 | Salmonella phage SETP3 | DNA polymerase | 524-3 | 258-431 | 141/174 (81%) | 3e-73 |
| | Salmonella phage KS7 | hypothetical protein | 524-3 | 258-431 | 141/174 (81%) | 3e-73 |
| | Enterobacteria phage SSL-2009a | DNA polymerase I | 524-48 | 259-438 | 104/195 (53%) | 2e-48 |
| 3 | Salmonella phage SETP3 | hypothetical protein | 3-440 | 36-181 | 144/146 (98%) | 9e-69 |
| | Salmonella phage KS7 | hypothetical protein | 3-440 | 23-168 | 144/146 (98%) | 1e-68 |
| | Salmonella phage KS7 | hypothetical protein | 555-1 | 180-364 | 175/185 (94%) | 4e-95 |
| | Salmonella phage SETP3 | hypothetical protein | 558-1 | 179-364 | 172/186 (92%) | 2e-94 |
| 4 | Salmonella phage KS7 | structural protein | 3-917 | 162-466 | 300/305 (98%) | 3e-174 |
| | Salmonella phage SETP3 | putative structural protein | 3-194 | 162-465 | 285/304 (93%) | 2e-174 |
| | Salmonella phage KS7 | structural protein | 915-253 | 272-491 | 189/221 (85%) | 3e-94 |
| | Salmonella phage SETP3 | putative structural protein | 915-277 | 272-481 | 164/213 (76%) | 4e-83 |
| 5 | Salmonella phage SETP3 | putative helicase | 2-811 | 384-653 | 258/270 (95%) | 1e-131 |
| | Salmonella phage KS7 | hypothetical protein | 2-811 | 37-306 | 259/270 (95%) | 2e-130 |
| | Salmonella phage SETP3 | putative helicase | 904-197 | 588-821 | 216/236 (91%) | 6e-109 |
| | Salmonella phage KS7 | hypothetical protein | 904-197 | 241-474 | 213/236 (90%) | 8e-108 |

EXAMPLE 7

PCR Analysis Using ΦCJ8-Specific Primers

Figure 5:
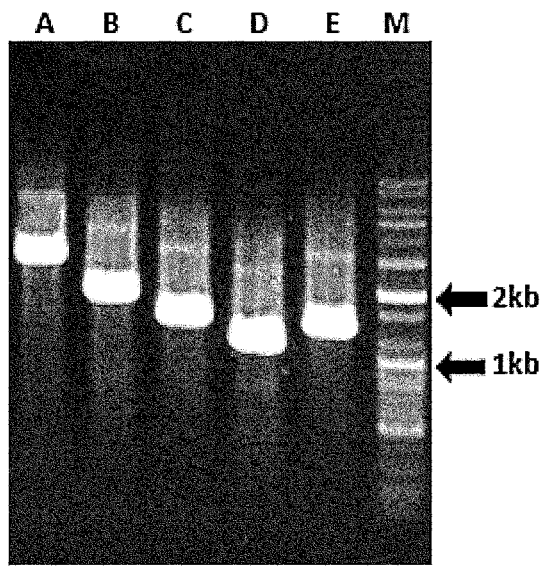
FIG. 5 is the result of PCR, performed using each primer set for the ΦCJ8 genomic DNA.
A: 3.5 kbp-long PCR product obtained with a primer set of SEQ ID NOs: 6 and 7;
B: 2.1 kbp-long PCR product obtained with a primer set of SEQ ID NOs: 8 and 9;
C, 1.6 kbp-long PCR product obtained with a primer set of SEQ ID NOs: 10 and 11;
D: 1.2 kbp-long PCR product obtained with a primer set of SEQ ID NOs: 12 and 13; and
E: 1.4 kbp-long PCR product obtained with a primer set of SEQ ID NOs: 14 and 15

In order to identify ΦCJ8, ΦCJ8-specific primers were designed on the basis of SEQ ID NOs: 1 to 5. PCR was performed using each primer set of SEQ ID NOs: 6 and 7, SEQ ID NOs: 8 and 9, SEQ ID NOs: 10 and 11, SEQ ID NOs: 12 and 13, and SEQ ID NOs: 14 and 15. 0.1 μg of the genomic DNA of bacteriophage and 0.5 pmol of each primer were added to pre-mix (Bioneer), and the final volume was adjusted to 20 μl. PCR was performed with 35 cycles of denaturation at 94° C. for 1 min, annealing at 52° C. for 1 min and polymerization at 72° C. for 1 min after initial denaturation at 94° C. for 10 min, followed by final amplification at 72° C. for 10 min. The PCR products thus obtained were approximately 3.5, 2.1, 1.6, 1.2 and 1.4 kbp long, respectively. The results are shown in FIG. 5.

EXAMPLE 8 pH Stability of ΦCJ8

Figure 6:
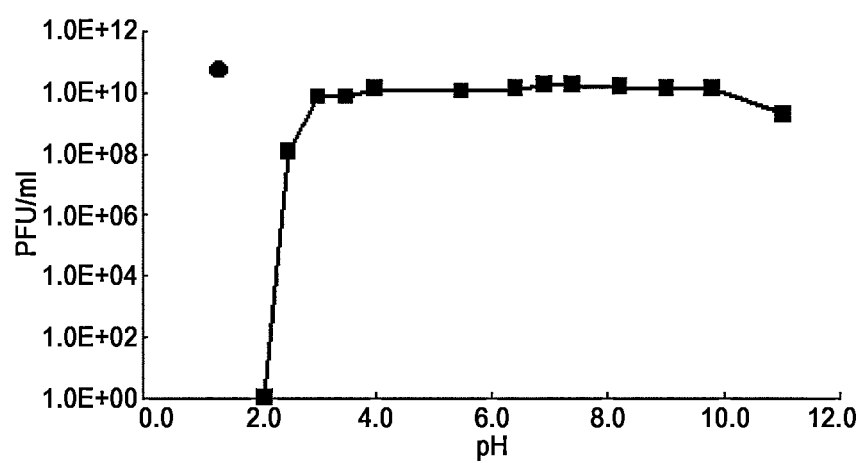
FIG. 6 is the result of acid-resistance assay on the bacteriophage ΦCJ8, showing the number of surviving bacteriophage at pH 2.1, 2.5, 3.0, 3.5, 4.0, 5.5, 6.4, 6.9, 7.4, 8.0, 9.0, 9.8 and 11.0. The bacteriophage ΦCJ8 did not lose its activity until pH 2.5, but completely lost it at pH 2.5 or lower, as compared to the control.

In order to determine whether ΦCJ8 survives at low pH environment in the stomach of livestock, its stability was assessed in a wide range of pH (pH 2.1, 2.5, 3.0, 3.5, 4.0, 5.5, 6.4, 6.9, 7.4, 8.2, 9.0, 9.8, 11.0). Various pH solutions (sodium acetate buffer (pH 2.1, 4.0, 5.5 and 6.4), sodium citrate buffer (pH 2.5, 3.0 and 3.5), sodium phosphate buffer (pH 6.9 and 7.4) and Tris-HCl (pH 8.2, 9.0, 9.8 and 11.0)) were prepared to have a concentration of 2 M. 180 μl of each pH solution was mixed with 20 μl of a bacteriophage solution ($1.1 \times 10^{11}$ pfu/Ml), followed by incubation at room temperature for 2 hr. The reaction solution was serially diluted, and 10 μl of each dilution was cultured at 37° C. for 18 hrs according to a soft agar overlay method, and the titration of phage lysates was performed. Changes in the titers according to pH difference were compared to examine the relative stability. The results showed that the bacteriophage did not lose its activity and maintained stability up to pH 3.0. However, it lost its activity at pH 2.5 or below. The results are shown in FIG. 6.

EXAMPLE 9

Heat Stability of ΦCJ8

Figure 7:
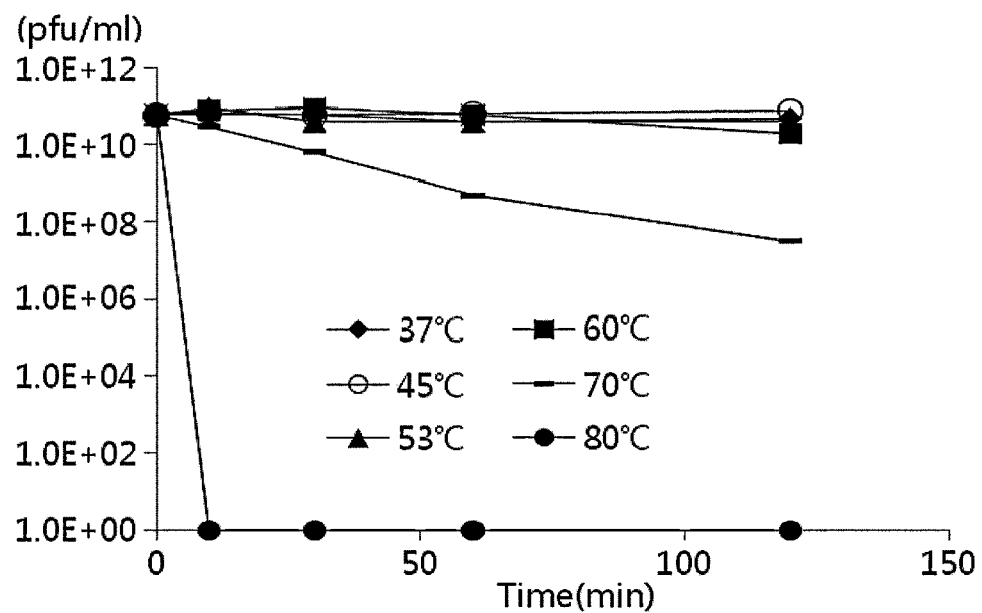
FIG. 7 is the result of heat-resistance assay on the bacteriophage ΦCJ8, showing the number of surviving bacteriophage at 37, 45, 53, 60, 70 and 80° C. and a time point of 0, 10, 30, 60 and 120 min. The bacteriophage ΦCJ8 retains its activity even after incubation at 60° C. for 2 hrs, but entirely loses it after incubation at 70° C. for 2 hrs.

To test stability of a bacteriophage to heat generated during formulation process when used as a feed additive, the following experiment was performed. 200 μl of a ΦCJ8 solution with a titer of $1.0 \times 10^{11}$ pfu/Ml was incubated at 37° C., 45, 53, 60, 70 and 80° C. for 0, 10, 30, 60, and 120 min, respectively. The solution was serially diluted, and 10 µl of each dilution was cultured at 37° C. for 18 hrs according to a soft agar overlay method, and the titration of phage lysates was performed. Changes in the titers according to temperature and exposure time were compared to examine the relative stability. The results showed that the bacteriophage retained its activity following incubation at 60° C. for 2 hours. However, the bacteriophage rapidly lost its activity following incubation at 80° C. for 10 minutes or longer. The results are shown in FIG. 7.

EXAMPLE 10

Desiccation Tolerance of ΦCJ8

Figure 8:
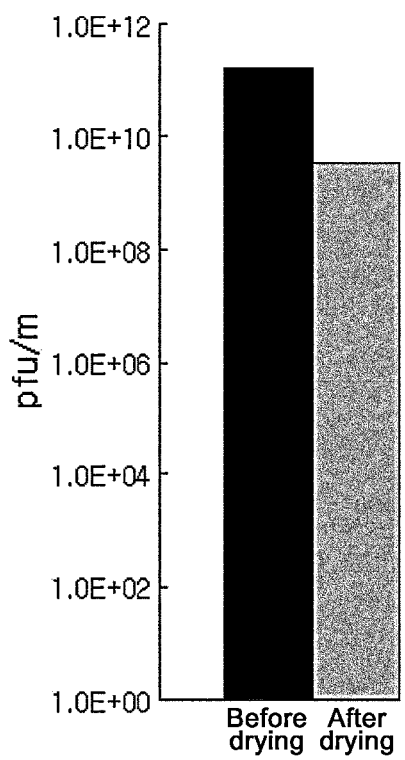
FIG. 8 is the result of desiccation resistance assay on the bacteriophage ΦCJ8, performed at 60° C. for 120 min with the aid of SpeedVec concentrator, in which when changes in viral titers before and after drying were compared to examine the relative stability, the activity was decreased about 50-fold.

To test stability of bacteriophage under the dry condition during formulation process when used as a feed additive, the following experiment was performed. On the basis of the results of heat stability test, the experiment was performed under high-temperature drying conditions (at 60° C. for 120 min). 200 µl of a ΦCJ8 solution ($6.0 \times 10^{11}$ pfu/Ml) was dried using a Speed vacuum (Speed-Vacuum Concentrator 5301, Eppendorf). The obtained pellet was completely resuspended in 200 µl of the SM solution at 4° C. for one day. The solution was serially diluted, and 10 µl of each diluted sample was cultured at 37° C. for 18 hours according to soft agar overlay method, and the titration of phage lysates was performed. Changes in the titers before and after drying were compared to examine the relative stability. The results showed that its activity was decreased by about 50-fold. The results are shown in FIG. 8.

EXAMPLE 11

Examination on Infection Spectrum of ΦCJ8 to Wile-Type Salmonella Strains

Besides SE (SCSG SE2282), ST (ATCC ST14028), SG (SGSC SG2293) and SP (SGSC SP2295), the lytic activity of ΦCJ8 was assayed for Korean wild-type SE (49 strains), ST (25 strains), SG (53 strains), SP (19 strains), SC (7 strains) and SD (3 strains), obtained from Laboratory of Avian Diseases, College of Veterinary Medicine, Seoul National University, and National Veterinary Research and Quarantine Service and the Korea Centers for Disease Control and Prevention.

150 µl of each strain shaking culture medium ($OD_{600}=2$) was mixed, and 10 µl of ΦCJ8 solution ($10^{10}$ pfu/Ml) was cultured at 37° C. for 18 hrs accorting to a soft agar overlay method, and the plaque formation was examined. It was found that the bacteriophage ΦCJ8 showed lytic activity of 95% against SE, ST, SG and SP. The results are summarized in Table 3.

TABLE 3

Lytic Activity of ΦCJ8 against Korean Wild-Type Strains SE, ST, SG and SP

| Sero type | Strain name | ΦCJ8 Plaque formation |
|---|---|---|
| SG | SNU SG1 | ○ |
|  | SNU SG2 | ○ |
|  | SNU SG3 | ○ |
|  | SNU SG4 | ○ |
|  | SNU SG5 | ○ |
|  | SNU SG6 | ○ |
|  | SNU SG7 | ○ |
|  | SNU SG8 | ○ |
|  | SNU SG9 | ○ |
|  | SNU SG10 | ○ |
|  | SNU SG11 | X |
|  | SNU SG12 | ○ |
|  | SNU SG13 | ○ |
|  | SNU SG14 | ○ |
|  | SNU SG15 | ○ |
|  | SNU SG16 | ○ |
|  | SNU SG17 | ○ |
|  | SNU SG18 | ○ |
|  | SNU SG19 | ○ |
|  | SNU SG20 | ○ |
|  | SNU SG21 | ○ |
|  | SNU SG22 | ○ |
|  | SNU SG23 | ○ |
|  | SNU SG24 | ○ |
|  | SNU SG25 | ○ |
|  | SNU SG26 | ○ |
|  | SNU SG27 | ○ |
|  | SNU SG28 | ○ |
|  | SNU SG30 | ○ |
|  | SNU SG31 | ○ |
|  | SNU SG32 | ○ |
|  | SNU SG33 | ○ |
|  | SNU SG34 | ○ |
|  | SNU SG36 | ○ |
|  | SNU SG37 | ○ |
|  | SNU SG38 | ○ |
|  | SNU SG39 | ○ |
|  | SNU SG40 | ○ |
|  | SNU SG41 | ○ |
|  | SNU SG42 | ○ |
|  | SNU SG43 | X |
|  | SNU SG44 | ○ |
|  | SNU SG45 | X |
|  | SNU SG46 | ○ |
|  | SNU SG47 | X |
|  | SNU SG48 | ○ |
|  | SNU SG49 | ○ |
|  | SNU SG50 | ○ |
|  | SGSC SG9184 | ○ |
|  | SGSC SG2292 | ○ |
|  | SGSC SG2293 | ○ |
|  | SGSC SG2744 | ○ |
|  | SGSC SG2296 | ○ |
| SP | SNU SP1 | ○ |
|  | SNU SP4 | ○ |
|  | SNU SP5 | ○ |
|  | SNU SP8 | ○ |
|  | SNU SP11 | ○ |
|  | SGSC SP2294 | ○ |
|  | SGSC SP2295 | ○ |
|  | SGSC SP2737 | X |
|  | SGSC SP2739 | ○ |
|  | SGSC SP2742 | ○ |
|  | SGSC SP2743 | ○ |
|  | SGSC SP2745 | ○ |
|  | SGSC SP2751 | ○ |
|  | SGSC SP4663 | ○ |
|  | SGSC SP4664 | ○ |
|  | SGSC SP4665 | ○ |
|  | SGSC SP4666 | ○ |
|  | SGSC SP4667 | ○ |
|  | SGSC SA1684 | ○ |
| SC | ATCC SC10708 | X |
|  | ATCC SC2929 | X |
|  | ATCC SC2930 | ○ |
|  | ATCC SC2931 | X |
|  | ATCC SC2932 | ○ |

TABLE 3-continued

Lytic Activity of ΦCJ8 against Korean Wild-Type Strains SE, ST, SG and SP

| Sero type | Strain name | ΦCJ8 Plaque formation |
|---|---|---|
| SE | ATCC SC2933 | ○ |
|  | ATCC SC2425 | ○ |
|  | SGSC SE2282 | ○ |
|  | SGSC SE2377 | ○ |
|  | PT4 S1400194 | ○ |
|  | PT4 LA52 | ○ |
|  | NVRQS SE004 | ○ |
|  | NVRQS SE005 | ○ |
|  | KCDC SE008 | ○ |
|  | KCDC SE009 | ○ |
|  | KCDC SE010 | ○ |
|  | KCDC SE011 | ○ |
|  | KCDC SE012 | ○ |
|  | KCDC SE013 | ○ |
|  | KCDC SE014 | ○ |
|  | KCDC SE015 | ○ |
|  | KCDC SE016 | ○ |
|  | KCDC SE017 | ○ |
|  | KCDC SE018 | ○ |
|  | KCDC SE019 | ○ |
|  | KCDC SE020 | ○ |
|  | KCDC SE021 | ○ |
|  | KCDC SE022 | ○ |
|  | KCDC SE023 | ○ |
|  | KCDC SE024 | ○ |
|  | KCDC SE025 | ○ |
|  | KCDC SE026 | ○ |
|  | KCDC SE027 | ○ |
|  | KCDC SE028 | ○ |
|  | KCDC SE029 | ○ |
|  | KCDC SE030 | ○ |
|  | KCDC SE031 | ○ |
|  | KCDC SE032 | ○ |
|  | KCDC SE033 | ○ |
|  | KCDC SE034 | ○ |
|  | KCDC SE035 | ○ |
|  | KCDC SE036 | ○ |
|  | KCDC SE037 | ○ |
|  | KCDC SE038 | ○ |
|  | KCDC SE039 | ○ |
|  | KCDC SE040 | ○ |
|  | KCDC SE041 | ○ |
|  | KCDC SE042 | ○ |
|  | KCDC SE043 | ○ |
|  | KCDC SE044 | ○ |
|  | KCDC SE045 | ○ |
|  | KCDC SE046 | ○ |
|  | KCDC SE047 | ○ |
|  | KCDC SE048 | ○ |
|  | KCDC SE049 | ○ |
|  | KCDC SE050 | ○ |
| ST | SNU ST1 | ○ |
|  | SNU ST2 | ○ |
|  | SNU ST3 | ○ |
|  | SNU ST4 | ○ |
|  | SNU ST7 | ○ |
|  | SNU ST8 | ○ |
|  | SNU ST11 | ○ |
|  | SNU ST12 | ○ |
|  | SNU ST13 | ○ |
|  | SNU ST14 | ○ |
|  | SNU ST17 | ○ |
|  | SNU ST18 | X |
|  | SNU ST19 | X |
|  | SNU ST20 | ○ |
|  | SNU ST25 | ○ |
|  | SNU ST26 | ○ |
|  | SNU ST37 | ○ |
|  | SNU ST38 | ○ |
|  | SNU ST41 | ○ |
|  | SNU ST42 | ○ |
|  | ATCC UK1 | ○ |
|  | ATCC 14028S | ○ |
|  | SGSC STM1412 | ○ |
|  | SGSC STM260 | ○ |
|  | SGSC STMSA2197 | ○ |
| SD | ATCC SD2466 | ○ |
|  | ATCC SD2467 | X |
|  | ATCC SD2468 | ○ |
| SA | ATCC 12398 | X |
| SB | ATCC 12397 | X |

\* SNU: Laboratory of Avian Diseases, College of Veterinary Medicine, Seoul National University
\* SGSC: Salmonella Genetic Stock Center
\* ATCC: The Global Bioresource Center
\* NVRQS: National Veterinary Research & Quarantine Service
\* KCDC: Korean Centers for Disease Control and prevention

EXAMPLE 12

Toxicity Assay of ΦCJ8

For safety use in the prevention of salmonellosis, *salmonella* food poisoning, fowl typhoid and pullorum, the bacteriophage was in vivo assayed for toxicity. Toxicity assay was performed with single oral dose. In this assay, rats were orally administered with a single dose of ΦCJ8 and monitored for acute toxicity to determine approximate lethal concentrations of ΦCJ8. Male and female (10 rats for each), 7-week-old, specific pathogen-free (SPF) rats were fasted one day before ΦCJ8 administration. On administration day, $1 \times 10^{13}$ pfu of ΦCJ8 was administered to male and female rats (5 rats for each) via an oral zonde, and a mixed solution of 20 mM Tris-HCl and 2 mM $MgCl_2$, was orally administered to 5 rats as a control group, after 4 hrs, to start refeeding. On administration day, the rats were examined 30 min after administration, and every 4 hours. For 14 days, clinical signs were examined and recorded once a day. As a result, there was no animal death, and clinical signs due to ΦCJ8 toxicity were not observed. The results are shown in Tables 4 to 6. Changes in body weight were measured and recorded before administration, and 1, 3, 7, 10 and 14 days after administration. As shown in FIG. 9, there was no significant change in body weight, as compared to the control group. The results indicate that ΦCJ8 does not induce any toxic reaction which causes loss of appetite or changes in body weight. Further, no noticeable abnormalities were found in any organ as examined by autopsy and with the naked eye. Therefore, the novel bacteriophage ΦCJ8 is non-toxic.

TABLE 4

Incidence of death after oral administration of ΦCJ8

| Sex | Done (pfu) | \multicolumn{14}{c}{Days after treatment} | No. Dead/No. Dosed |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | |
| Male | Control | 0 | 0 | 0 | 0 | 0 | 0 | 0 | 0 | 0 | 0 | 0 | 0 | 0 | 0 | 0/5 |
| | $10^{13}$ | 0 | 0 | 0 | 0 | 0 | 0 | 0 | 0 | 0 | 0 | 0 | 0 | 0 | 0 | 0/5 |
| Female | Control | 0 | 0 | 0 | 0 | 0 | 0 | 0 | 0 | 0 | 0 | 0 | 0 | 0 | 0 | 0/5 |
| | $10^{13}$ | 0 | 0 | 0 | 0 | 0 | 0 | 0 | 0 | 0 | 0 | 0 | 0 | 0 | 0 | 0/5 |

TABLE 5

Clinical signs after oral administration of ΦCJ8

| | | Final mortality | | Clinical signs | |
|---|---|---|---|---|---|
| Sex | Done (pfu) | Male | Female | Male | Female |
| Male | Control | 0/5 | 0/5 | 0/5 | 0/5 |
| | $10^{13}$ | 0/5 | 0/5 | 0/5 | 0/5 |
| Female | Control | 0/5 | 0/5 | 0/5 | 0/5 |
| | $10^{13}$ | 0/5 | 0/5 | 0/5 | 0/5 |

TABLE 6

Organ abnormality after oral administration of ΦCJ8

| Sex | Done (pfu) | gross finding | Frequency [A] |
|---|---|---|---|
| Male | Control | No gross finding | 5/5 |
| | $10^{13}$ | No gross finding | 5/5 |
| Female | Control | No gross finding | 5/5 |
| | $10^{13}$ | No gross finding | 5/5 |

[A] Number of animals with the sign/Number of animals examined.

EXAMPLE 13

Efficiency of ΦCJ8 as Feed Additive

In order to examine safety and preventive effect of ΦCJ8 on *Salmonella* for use as a feed additive, growth performance and relative weights of organs and muscles were measured. In this experiment, a total of 320 male broilers, 2-day-old Ross chicks (average body weight of 41.4 g) were used for 5 weeks of feeding trial. They were allotted to 4 treatments (control: basal diet, BP-1: basal diet+ΦCJ8 0.05%, BP-2: basal diet+ΦCJ8 0.10%, BP-3: basal diet+ΦCJ8 0.20%) with 8 replicates and 10 chicks per pen in randomized complete block (RCB) design. At this time, ΦCJ8 had a titer of $10^9$ pfu/g. The following experiment was conducted with corn-soy based diet and two phase feeding programs were used. In phase I, diet containing 23.0% crude protein and 1.19% lysine was supplied for 2 weeks. In phase II, diet containing 21.0% crude protein and 1.05% lysine was supplied for last 3 weeks. All other nutrients were met or exceeded requirements of Korean Feeding Standard for Poultry (2007).

As a result, the ΦCJ8 supplementation in broiler feed during 5 weeks of feeding trial did not cause any negative effect on growth performance in broiler chickens (Table 7). There was no significant difference in relative weights of organs such as liver, spleen, abdominal fat, breast muscle, and leg muscle, and muscles among treatments (Table 8). These results indicate that supplementation of ΦCJ8 did not induce any negative effect on growth performance or development of organs and muscles in broilers at a concentration of 0.05 to 0.2%. The continuous ΦCJ8 supplement during 5 weeks from breeding to shipment of broiler chicks did not show any negative effect on growth performance or development of organs and muscles in broilers, which confirms the safety of ΦCJ8. These results suggest that food poisoning caused by *Salmonella enteritidis* can be prevented in consumers of chickens fed with ΦCJ8 supplement owing to its specific bactericidal activity against the pathogen.

TABLE 7

Effect of ΦCJ8-supplemented feed on growth performance in broiler chickens

| | Treatment[A] | | | | |
|---|---|---|---|---|---|
| Criteria | CON | BP-1 | BP-2 | BP-3 | SEM[B] |
| Liver weight (g/bird) | | | | | |
| Initial | 41.4 | 41.4 | 41.4 | 41.4 | 0.03 |
| 2 week | 382.1 | 369.6 | 379.6 | 375.6 | 2.68 |
| 5 week | 1,988.40 | 1,959.00 | 1,999.90 | 1,991.10 | 10.64 |
| BW gain (g/bird) | | | | | |
| 0-2 week | 340.7 | 328.2 | 338.4 | 334.3 | 2.69 |
| 2-5 week | 1,606.30 | 1,589.50 | 1,620.30 | 1,615.50 | 9.28 |
| 0-5 week | 1,947.00 | 1,917.70 | 1,958.60 | 1,949.70 | 10.64 |
| Feed intake (g/bird) | | | | | |
| 0-2 week | 483.7 | 471.7 | 476.4 | 481.9 | 2.73 |
| 2-5 week | 2,727.30 | 2,740.70 | 2,789.60 | 2,728.90 | 20.35 |
| 0-5 week | 3,210.90 | 3,212.40 | 3,266.00 | 3,210.70 | 21.69 |
| FCR (F/G ratio) | | | | | |
| 0-2 week | 1.42 | 1.44 | 1.41 | 1.45 | 0.01 |
| 2-5 week | 1.7 | 1.73 | 1.72 | 1.69 | 0.01 |
| 0-5 week | 1.65 | 1.68 | 1.67 | 1.65 | 0.01 |

[A] Control (basal diet), BP-1 (basal diet + ΦCJ8 0.05%), BP-2 (basal diet + ΦCJ8 0.10%), BP-3 (basal diet + ΦCJ8 0.20%).
[B] Standard error of mean

TABLE 8

Effect of ΦCJ8-supplemented feed on relative weights of organs and muscles in broiler chickens

| | Treatment[A] | | | | |
|---|---|---|---|---|---|
| criteria | CON | BP-1 | BP-2 | BP-3 | SEM[B] |
| Liver, g/100 g BW | 1.88 | 1.93 | 1.77 | 1.79 | 0.16 |
| Spleen, g/100 g BW | 0.08 | 0.08 | 0.08 | 0.07 | 0.01 |
| Abdominal fat, g/100 g BW | 2.23 | 2.22 | 2.31 | 2.15 | 0.14 |
| Breast muscle, g/100 g BW | 7.8 | 7.64 | 7.57 | 7 | 0.23 |
| Leg muscle, g/100 g BW | 9.31 | 9.43 | 9.44 | 9.47 | 0.09 |

[A] Control (basal diet), BP-1 (basal diet + ΦCJ8 0.05%), BP-2 (basal diet + ΦCJ8 0.10%), BP-3 (basal diet + ΦCJ8 0.20%).
[B] Standard error of mean

EXAMPLE 14

Inhibitory Effects of ΦCJ8 on SE Propagation and Fecal Shedding

In order to examine the potential of ΦCJ8 for preventing or treating *Salmonella*, its inhibitory effects were evaluated in chickens. The efficacy test was performed on 270 parent stocks in a poultry farm under strict control for *Salmonella*. 270 day-old layers were divided into three treatment groups and a positive control group (60 chicks per group), and a negative control group (30 chicks), and each group was bred separately.

The three ΦCJ8 treatment groups were administered with feed containing ΦCJ8 at a concentration of $10^5$, $10^7$ and $10^9$ pfu/kg, respectively, and the positive and negative groups were fed with normal feed. Among 60 chicks of each treatment group, 30 chicks were orally challenged with SE (*Salmonella enteritidis*: $5 \times 10^7$ CFU/bird)("challenge group"), and the rest 30 chicks were bred with the treatment group challenged with SE ("contact-infected group"). At 7, 14, and 21 days after challenge with SE, SE was isolated from the cecal feces of each 10 chicks of the challenge group and the contact-infected group and a quantitative analysis was performed. At 7, 14, and 21 days after challenge with SE, samples were collected from the entrance door, floor, and ventilation filter in chicks' facility of the treatment and control groups, and the quantitative *salmonella* isolation was compared to each other.

At 7, 14, and 21 days after challenge with SE, the reduction of intestinal *salmonella* was observed in the challenge groups administered with ΦCJ8 of $10^7$ and $10^9$ pfu/kg and their contact-infected groups, compared to the positive control group. The treatment groups administered with ΦCJ8 of $10^7$ and $10^9$ pfu/kg showed a reduction in environmental contamination by SE, compared to the non-treated groups, implying that the bacteriophage ΦCJ8 of the present invention inhibits SE excretion to environment. The ΦCJ8 administration also inhibited SE proliferation in intestines of the challenge group, which results in a decrease in SE excretion to environment, consequently leading to the block of SE propagation into the contact-infected group bred therewith. The results are shown in Tables 9 and 10.

TABLE 9

Inhibitory Effect of Feed Additive ΦCJ8 on SE Propagation

| | | | Quantitative analysis of SE isolated from cecal feces after oral challenge with SE (CFU/g)[A] | | |
|---|---|---|---|---|---|
| | Challenge | No | 7 dpc[B] | 14 dpc | 21 dpc |
| Treatment ($10^9$ pfu/kg)[C] | Challenge group[D] | 30 | 3.41E+05 | 3.06E+05 | 2.68E+04 |
| | Contact-infected group[E] | 30 | 3.00E+04 | 2.90E+04 | 1.41E+04 |
| Treatment ($10^7$ pfu/kg) | Challenge group | 30 | 5.03E+05 | 1.58E+06 | 7.21E+04 |
| | Contact-infected group | 30 | 1.68E+04 | 8.19E+05 | 4.73E+04 |
| Treatment ($10^5$ pfu/kg) | Challenge group | 30 | 3.58E+05 | 3.18E+06 | 1.27E+05 |
| | Contact-infected group | 30 | 1.41E+05 | 1.47E+06 | 5.08E+05 |
| Non-treatment[F] | Challenge group | 30 | 2.48E+06 | 3.55E+06 | 6.23E+05 |
| | Contact-infected group | 30 | 1.62E+05 | 1.75E+06 | 5.01E+05 |
| Negative control[G] | | 30 | 0 | 0 | 0 |

[A] Quantitative *salmonella* isolation from cecal feces for 3 weeks after oral challenge with SE
[B] Day post challenge
[C] Group administered with ΦCJ8 as feed additive
[D] Challenge group orally challenged with SE
[E] Contact-infected group bred with SE challenged group
[F] Non-treated group fed with normal feed supplemented with no ΦCJ8
[G] Negative control group not challenged with SE after feeding with normal feed supplemented with no ΦCJ8

TABLE 10

Inhibitory Effect of ΦCJ8 on SE excretion

Quantitative analysis of SE in environmental samples after oral challenge with SE

| | 7 dpc[B] | | | |
|---|---|---|---|---|
| | Entrance door | Floor | Ventilation filter | Total |
| Treatment ($10^9$ pfu/kg)[C] | 2/2 | 1/2 | 0/2 | 3/6 (50) |
| Treatment ($10^7$ pfu/kg) | 2/2 | 0/2 | 0/2 | 2/6 (33) |
| Treatment ($10^7$ pfu/kg) | 2/2 | 1/2 | 1/2 | 4/6 (66) |
| Non-treatment[D] | 2/2 | 2/2 | 1/2 | 5/6 (33) |
| Negative-control[E] | 0/2 | 0/2 | 0/2 | 0/6 (0) |

| | 14 dpc | | | |
|---|---|---|---|---|
| | Entrance door | Floor | Ventilation filter | Total |
| Treatment ($10^9$ pfu/kg)[C] | 1/2 | 2/2 | 0/2 | 3/6 (50) |
| Treatment ($10^7$ pfu/kg) | 2/2 | 1/2 | 0/2 | 3/6 (50) |
| Treatment ($10^7$ pfu/kg) | 2/2 | 2/2 | 1/2 | 5/6 (33) |
| Non-treatment[D] | 2/2 | 2/2 | 1/2 | 5/6 (33) |
| Negative-control[E] | 0/2 | 0/2 | 0/2 | 0/6 (0) |

| | 21 doc | | | |
|---|---|---|---|---|
| | Entrance door | Floor | Ventilation filter | Total |
| Treatment ($10^9$ pfu/kg)[C] | 1/2 | 0/2 | 0/2 | 1/6 (16) |
| Treatment ($10^7$ pfu/kg) | 2/2 | 0/2 | 1/2 | 3/6 (50) |
| Treatment ($10^7$ pfu/kg) | 2/2 | 1/2 | 1/2 | 4/6 (66) |
| Non-treatment[D] | 2/2 | 2/2 | 2/2 | 5/6 (33) |
| Negative-control[E] | 0/2 | 0/2 | 0/2 | 0/6 (0) |

[A] *Salmonella* isolation from environmental samples at 1, 2, and 3 weeks after challenge with SE
[B] Day post challenge
[C] Group administered with ΦCJ8 as feed additive
[D] Non-treated group fed with normal feed supplemented with no ΦCJ8
[E] Negative control group not challenged with SE after feeding with normal feed supplemented with no ΦCJ8

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isolated bacteriophage having a specific bactericidal activity against one or more *Salmonella* bacteria selected from the group consisting of *Salmonella enteritidis, Salmonella typhimurium, Salmonella gallinarum* and *Salmonella pullorum*, which is deposited under accession number KCCM11148P.

2. A composition for reduction or treatment of infectious diseases caused by one or more *Salmonella* bacteria selected from the group consisting of *Salmonella enteritidis, Salmonella typhimurium, Salmonella gallinarum*, and *Salmonella pullorum*, comprising the bacteriophage of claim 1 as an active ingredient.

3. The composition according to claim 2, wherein the infectious disease caused by *Salmonella enteritidis* or *Salmonella typhimurium* is salmonellosis and *Salmonella* food poisoning, the infectious disease caused by *Salmonella gallinarum* is Fowl typhoid, and the infectious disease caused by *Salmonella pullorum* is Pullorum disease.

4. An antibiotic composition for reduction or treatment of infectious diseases caused by one or more *Salmonella* strains selected from the group consisting of *Salmonella enteritidis, Salmonella typhimurium, Salmonella gallinarum*, and *Salmonella pullorum*, comprising the bacteriophage of claim 1 as an active ingredient.

5. An animal feed or drinking water, comprising the bacteriophage of claim 1 as an active ingredient.

6. A sanitizer or cleaner, comprising the bacteriophage of claim 1 as an active ingredient.

7. A method for reducing or treating infectious diseases caused by one or more *Salmonella* strains selected from the group consisting of *Salmonella enteritidis, Salmonella typhimurium, Salmonella gallinarum*, and *Salmonella pullorum*, comprising administering the bacteriophage of claim 1 to animals in need thereof.

8. A method for reducing or treating infectious diseases caused by one or more *Salmonella* strains selected from the group consisting of *Salmonella enteritidis, Salmonella typhimurium, Salmonella gallinarum*, and *Salmonella pullorum*, comprising administering the composition of claim 7 to animals in need thereof.

* * * * *